United States Patent [19]

Batzar

[11] 4,079,621
[45] Mar. 21, 1978

[54] APPARATUS FOR DETERMINING THE DUST INDEX OF A PARTICULATE SOLID

[75] Inventor: Kenneth Batzar, Piscataway, N.J.

[73] Assignee: E. I. Du Pont de Nemours and Company, Wilmington, Del.

[21] Appl. No.: 741,724

[22] Filed: Nov. 15, 1976

Related U.S. Application Data

[62] Division of Ser. No. 690,937, May 28, 1976.

[51] Int. Cl.² .............................................. G01N 1/22
[52] U.S. Cl. ...................................... 73/28; 73/432 R
[58] Field of Search ................ 73/432 R, 28, 421.5 A, 73/421.5 R; 55/270

[56] References Cited

U.S. PATENT DOCUMENTS 3,677,065  7/1972  Davis ..................................... 73/28
3,957,469  5/1976  Nebash .............................. 73/28 X

FOREIGN PATENT DOCUMENTS 1,164,126  5/1961  Germany .................................. 73/28
1,343,963  1/1974  United Kingdom ..................... 73/28

Primary Examiner—Richard C. Queisser
Assistant Examiner—Joseph W. Roskos

[57] ABSTRACT

Apparatus for collecting the dust arising from a particulate solid comprising a first container with a porous member fitted to an opening therein, a rotatable shaft, transversely mounted inside the first container and supporting a second container, which holds a particulate solid and a means for applying a vacuum to the opening in the first container. In practice, the second container is rotated pouring out the particulate solid and the airborn particles are drawn to the porous member by application of vacuum.

1 Claim, 2 Drawing Figures

U.S. Patent    March 21, 1978    4,079,621
FIG. 1
FIG. 2
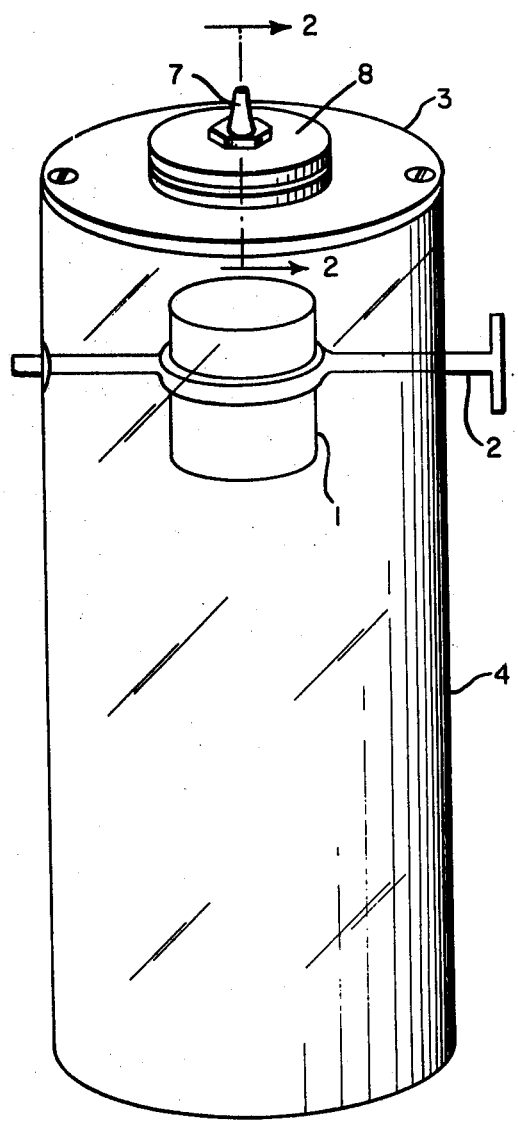
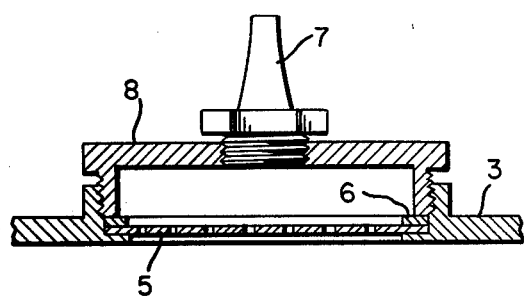

APPARATUS FOR DETERMINING THE DUST INDEX OF A PARTICULATE SOLID

CROSS REFERENCE TO RELATED APPLICATION

This application is a division of my copending application Ser. No. 690,937, filed May 28, 1976.

BACKGROUND OF THE INVENTION

This invention relates to metal chromate pigment compositions, and, more particularly, to substantially non-dusting metal chromate pigment compositions and their preparation.

Metal chromate pigments have been known and widely used for many years, and are available in a broad range of shades from very green shade yellows to yellowish reds. Of the various metal chromate pigments, e.g., strontium chromate, zinc chromate, and lead chromate, lead chromate is the most widely used. These chromate pigments are relatively inexpensive to manufacture and have generally good tinctorial properties.

Thermal stability and chemical resistance of metal chromate pigments have been improved markedly by the application of coatings of hydrous oxides such as silica and alumina to the base or uncoated metal chromate pigment, as described for example in Linton U.S. Pat. No. 3,370,971. To improve the mechanical strength of the coated metal chromate pigments, alkaline earth metal salts of rosin acids and of long-chain fatty acids have been applied to the pigments, as described in Linton U.S. Pat. No. 3,470,007.

Metal chromate pigments, though manufactured in aqueous systems, are commonly dried to a powder prior to shipment and use in coating compositions. Packaging, pouring and otherwise handling the dry pigment can create a dusting problem in the immediate work environment. If the dust level is sufficiently high, special protective equipment may be necessary to insure proper worker safety. With increased industry and government concern over protection of the environment and worker health, it is highly desirable to have a dry chromate pigment which is substantially dust-free. The resulting elimination of the need for special protective equipment can cut the cost of pigment to the manufacturer and user and insure worker safety with less monitoring and inconvenience than is currently employed.

This invention provides for substantially dust-free metal chromate pigment which exhibits all the desirable properties common to conventional metal chromate pigments.

SUMMARY OF THE INVENTION

According to this invention there is provided a metal chromate pigment composition consisting essentially of from 75% to 98% by weight, and preferably from 85% to 92% by weight, of a metal chromate pigment, based on the weight of the metal chromate pigment composition and from 2% to 25% by weight, and preferably from 8% to 15% by weight, based on the weight of metal chromate pigment composition, of at least one organic ester selected from esters of phthalic and terephthalic acid of the formula

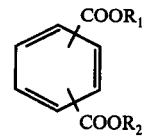

where $R_1$ and $R_2$ are each independently selected from alkyl of 3 to 20 carbon atoms, benzyl of the formula

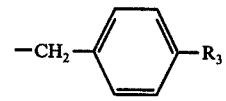

where $R_3$ is selected from —H, —SO$_3$H, and

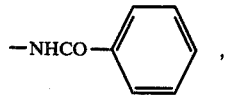

and esters of fatty acids of the formula

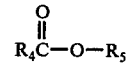

where $R_4$ is alkyl of 5 to 20 carbon atoms and $R_5$ is an alkyl of 2 to 10 carbon atoms.

The metal chromate pigment composition is preferably prepared by the steps of i. forming a mixture consisting essentially of from 1% to 80% by weight of metal chromate pigment, based on the weight of the mixture, and from 20% to 99% by weight of water, based on the weight of the mixture, ii. intimately contacting the mixture of step (i) with from 2% to 25% by weight, based on the weight of the metal chromate pigment, of at least one organic ester selected from esters of phthalic and terephthalic acid of the formula

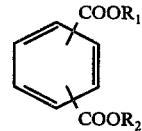

where $R_1$ and $R_2$ are each independently selected from alkyl of 3 to 20 carbon atoms, benzyl of the formula

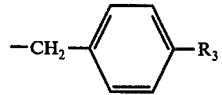

where $R_3$ is selected from —H, —SO$_3$H, and

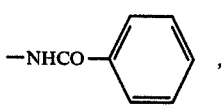

and esters of fatty acids of the formula

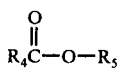

where $R_4$ is alkyl of 5 to 20 carbon atoms and $R_5$ is an alkyl of 2 to 10 carbon atoms.

iii. isolating the metal chromate pigment composition.

This invention further provides for an apparatus for determining, either qualitatively or quantitatively, the level of dust which arises from a given quantity of dry particulate solid, referred to herein as the dust index, comprising a first container having an opening in the top, a porous member detachably fitted to the opening in the top of the first container, a rotatable shaft, mounted transversely with respect to the first container, supporting a second container, the second container being smaller than the first container and coaxially disposed with respect to the first container, the axis of the shaft being positioned between the top of the first container and the bottom of the first container to allow the second container to rotate within the first container, and means for applying a vacuum to the opening in the top of the first container.

DESCRIPTION OF THE DRAWING

FIG. 1 — apparatus for determining the dust index of a particulate solid.

FIG. 2 — cross-sectional view of the top of the apparatus.

DETAILED DESCRIPTION OF THE INVENTION

The metal chromate pigments included in the composition of the invention are strontium chromate, zinc chromate and lead chromate, in the form of base or uncoated pigment including the known aftertreatment of hydrous oxides, metal salts of rosin acids or metal salts of long-chain fatty acids. Lead chromate pigments are preferred because of their widespread use in the industry and their excellent tinctorial properties. The preferred lead chromate pigments are available in a broad range of shades. On the one hand there is a very green shade "Primrose Yellow" in rhombic crystal form. A relatively pure lead chromate in monoclinic crystal form is much redder and is commonly known as "Medium Yellow". Intermediate shades of lead chromate pigment are available in solid solutions of lead chromate and lead sulfate usually in monoclinic form. At the other color extreme is a series of solid solutions of lead chromate, lead sulfate and lead molybdate which are oranges or even yellowish reds commonly known as "Molybdate Oranges" or "Molybdate Reds".

The organic ester component of the compositions of the invention which are preferred include dialkyl esters of phthalic acid wherein the alkyl groups contain 4 to 8 carbon atoms, such as di-2-ethylhexyl phthalate, and alkyl benzyl esters of phthalic acid, such as butyl benzyl phthalate. The preferred esters of fatty acids contain from 12 to 18 carbons in the alkyl group of the fatty acid and from 3 to 8 carbon atoms in the ester alkyl group, such as butyl stearate. The amount of organic ester in the composition varies according to the particular ester employed and the end use for which the pigment composition is intended. For example, if the pigment composition is to be used as a colorant for plastics, where only a relatively small quantity of pigment is commonly used, as high as 25% by weight of organic ester can be present in the pigment composition. In practice, it is preferred for most uses that the pigment composition contain at least 2% by weight of at least one organic ester to render the dry particulate solid substantially dust-free. Using more than 25% by weight of organic ester contributes little, if any, to the further decrease in dusting and is not recommended. Such higher levels may adversely affect the properties of the metal chromate pigment composition in use and cause the formation of plastic-like masses if the pigment composition is pulverized. For most applications 10% to 15% by weight of organic ester is preferred.

To insure that the metal chromate pigment composition of the invention remains substantially dust-free during dry handling, the melting point of the organic ester or mixture of organic esters which are present in the composition should be below the temperature at which the composition is handled in the dry state. In most cases the dry composition is handled at ambient temperature, e.g., 15° C.–25° C. Consequently, a melting point of 15° C. or less is satisfactory for the organic ester component of the composition.

In the event that the melting point of a particular organic ester of choice is higher than desired, mixtures of esters can be formulated within the level of one skilled in the art to lower the melting point of the organic ester component to the desired level. For example, the melting point of n-butyl stearate is 19° C.–24° C., which may be too high for many work environments. A mixture of n-butyl stearate and isobutyl stearate which has a melting point several degrees lower will exhibit this melting point depression depending upon the relative amounts of each component used. The same is true for di-n-octylphthalate versus a mixture of di-n-octylphthalate and di-2-ethylhexyl phthalate.

To prepare the metal chromate pigment composition of the invention a mixture of metal chromatic pigment in aqueous medium is intimately contacted with at least one organic ester, preferably from 10% to 15% by weight, based on the weight of the metal chromate pigment. The relative amounts of pigment and water can be such that the mixture is in the form of an aqueous slurry of pigment, for which the mixture can contain from 1% to 35% by weight of pigment, based on the weight of the mixture and from 65% to 99% by weight of water, based on the weight of the mixture. Alternatively the mixture can be in the form of an aqueous presscake which, for example, normally results when the metal chromate pigment is isolated by filtration from the aqueous medium in which it was synthesized. In the case of a presscake, the mixture can contain from 25% to 80% by weight of metal chromate pigment, based on the weight of the mixture, and from 20% to 75% of water, based on the weight of the mixture.

Formation of the metal chromate pigment composition is best achieved by promoting intimate contact of the pigment/water mixture and the organic ester. Intimate contact can be conveniently and effectively achieved by subjecting the pigment/water mixture and the organic ester to agitation, stirring or emulsification. Common devices to effect such contact include conventional blenders, and, in general, containers equipped with high speed agitators. The organic ester can be contacted with the pigment/water mixture as such or the organic ester can first be emulsified in water prior to contact with the pigment/water mixture. The latter procedure is preferred as it insures homogeneous distribution of the organic ester throughout the metal chromate pigment.

Although the temperature of contact is not particularly critical, it is preferred that the temperature be from 80° C. to 95° C. to insure complete association of the organic ester with the metal chromate pigment. This temperature range is further preferred for the sake of convenience, since the aqueous pigment slurries in which metal chromate pigments are synthesized are commonly within this temperature range prior to isolation of the pigment. Consequently, without first isolating the pigment from the synthesis slurry, the pigment slurry can be directly used in the process of the invention to prepare the metal chromate pigment composition.

As stated above the metal chromate pigment composition can be prepared directly from a synthesis slurry of base or uncoated pigment or of coated pigment. A major factor governing the point during the processing of the pigment where formation of the pigment composition is desirable is the point at which the pigment is handled dry and dust control is a problem. For example, when the base or uncoated pigment is isolated from the synthesis slurry and dried prior to application of a coating, e.g., silica, the pigment composition should preferably be formed prior to drying and subsequent application of the coating. The practice of the invention does not interfere with the subsequent application of coating or other conventional aftertreatments. To insure dust control after further processing of the pigment, e.g., application of coating, it is preferred that the further processed or coated pigment again be mixed with water and intimately contacted with an organic ester in accordance with the invention.

The metal chromate pigment composition, in which pigment and organic ester are believed to form cohesive discrete particles of the composition, can be isolated from the aqueous slurry in any conventional manner. For example, the slurry can be flocculated, if necessary, with such flocculating agents as aluminum sulfate, filtered, washed with water and dried at ambient or elevated temperatures.

The isolated dry metal chromate pigment composition can be packaged, poured, or otherwise handled without substantial formation of dust.

To determine the level of dusting or dust index of the dry particulate metal chromate pigment composition, and the level of dusting of particulate solids generally, the device shown in FIGS. 1 and 2 is utilized. Referring to FIG. 1, a quantity of particulate solid is placed in internal container 1 which is mounted to rotatable shaft 2. A housing 3 for a porous member and nozzle for a vacuum line is securely attached to cover the opening in external container 4. FIG. 2 shows a cross-sectional view of housing 3. Referring to FIG. 2, porous member 5 is placed in the opening in housing 3. The size of the pores in the porous member should be small enough to prevent passages therethrough of particles of the solid to be tested. For the metal chromate pigment composition of the invention conventional white filter paper e.g., Whatman #2, is preferred. To insure that the filter paper remains in place during the determination, a metal ring 6, is placed on top of the filter paper. A nozzle 7 is then attached to nozzle housing 8 which is securely fitted to housing 3. A vacuum line, not shown, can be attached to nozzle 7.

To determine the dust index the internal container 1 is rapidly inverted by rotating the shaft 2. Three seconds after inverting the container a vacuum of from 55 to 65 mm of Hg is drawn for 10 seconds on the external container 4 through nozzle 7. In this manner the particulate solid which is still suspended in the atmosphere of the external container 1 is drawn to the porous member 5 and is deposited thereon as the vacuum is drawn. The nozzle housing 8 is then removed from the top of external container 4 and the porous member is removed. A relatively accurate and highly reproducible qualitative determination of the dust index can be determined by visual examination of the porous member. Since the metal chromate pigment composition is highly colored, even minute quantities will impart some color to the porous member. A highly colored porous member is indicative of a high dust index whereas a very faintly colored or noncolored porous member is indicative of a low dust index; in other words a substantially dust-free particulate solid.

Although it is believed that the qualitative determination described above is a highly satisfactory indication of a given dust index, the amount of dust generated by a given quantity of pigment can of course be determined by destruction of the filter paper and pigment with subsequent analysis, for example, by atomic absorption. In any case, comparative determinations should be made using the same amount of particulate solid, same hold time after inversion of the internal container, and same amount of vacuum to provide a controlled comparison.

When tested for dusting as described above, the metal chromate pigment composition of the invention shows at most only very faint coloration of the porous member and is consequently substantially dust-free. Metal chromate pigments known in the art show extreme coloration of the porous member when comparably tested.

Like conventional metal chromate pigments, the metal chromatic pigment composition of the invention is useful as a pigment for a wide variety of applications. For example the composition can be directly incorporated in plastics or coating compositions, such as oil or water base paints in the conventional manner to impart color thereto.

The following examples are to illustrate the invention.

EXAMPLE 1

Forty-eight hundred milliliters of an aqueous slurry containing 480 grams of lead chromate pigment of the molybdate orange type coated with 16% by weight of dense amorphous silica is heated to 90° C. In a separate container 10.15 grams of a commercially available non-ionic surfactant is dissolved in 67.5 grams of dioctyl phthalate. The solution of di-2-ethylhexyl phthalate and surfactant is then added to 350 milliliters of hot water at a temperature of 60° C. in a high-speed blender. The resulting mixture is emulsified at low speed and added slowly with stirring to the heated aqueous slurry prepared above. The slurry is stirred for 15 minutes after the completion of the addition. Then 30 grams of aluminum sulfate is added to the slurry to effect flocculation and the pH is adjusted to 4.0–4.2.

To isolate the product the flocculated slurry is filtered, washed with water to a specific resistance of 5000 ohm-cm and dried at 82° C for 16 hours. The dried product is then pulverized at high speed using a 0.066 screen and yields 546 grams of bright orange pigment.

The product contains 13% by weight of di-2-ethylhexyl phthalate and 87% by weight of lead chromate pigment.

Using the apparatus pictured in FIG. 1, 45 grams on a pigment basis of the lead chromate pigment composition is placed in internal container 1, diameter 5.5 cm. and height 5.5 cm. A filter paper, i.e., Whatman No. 2, and vacuum line are attached to the opening in external container 4, diameter 14 cm. and height to opening 6.35 cm. The internal container 1 is inverted by turning shaft 2, located 24 cm. from the bottom of external container 4. Three seconds after inversion of internal container 1 a vacuum of 60 mm Hg is applied to external container 4 for 10 seconds. The filter paper is then removed and found to exhibit no visible coloration.

CONTROL A

The procedure of Example 1 is followed except that no dioctyl phthalate solution is added to the slurry. The resulting lead chromate pigment is tested exactly as described in Example 1 and the resulting filter paper shows very intense coloration.

EXAMPLE 2

Fifty-one hundred milliliters of an aqueous slurry containing 600 grams of yellow lead chromate pigment is heated to 90° C. In a separate container 13 grams of the surfactant described in Example 1 is dissolved in 65 grams of dioctyl phthalate and emulsified as described in Example 1. The emulsion is added dropwise to the aqueous slurry of pigment over a 2-minute period. Then 75 milliliters of a commercially available polyacrylamide flocculating agent is added to the slurry to effect flocculation.

To isolate the product the flocculated slurry is filtered, washed with water to a specific resistance of 1200 ohm-cm and dried at 104° C. The product is pulverized as described in Example 1 and yielded 662 grams of bright yellow pigment. The product contains 10% by weight of dioctyl phthalate and 90% by weight of yellow lead chromate pigment.

The lead chromate pigment composition is tested exactly as described in Example 1 and the resulting filter paper exhibits very faint yellow coloration.

CONTROL B

The procedure of Example 2 is followed except that no dioctyl phthalate solution is added to the slurry. The resulting lead chromate pigment is tested exactly as described in Example 1 and the resulting filter paper shows very intense yellow coloration.

EXAMPLE 3

One hundred milliliters of water containing 4.5 grams of a commercially available non-ionic surfactant in solution is added dropwise to 30 grams of dibutyl phthalate with agitation and stirred for 5 minutes. The resulting solution is added to a high-speed blender. An aqueous presscake (35–40% by weight of water) containing 150 grams, dry basis, of a lead chromate of the molybdate orange type described in Example 1 is added to the high-speed blender and blended for 10 minutes. The blended mixture is dried at 82° C for 16 hours and pulverized at high speed using a 0.066 screen.

The resulting bright orange pigment composition is tested for dust as described in Example 1 and the filter paper exhibits no visible coloration.

CONTROL C

The procedure of Example 3 is followed except that the presscake is not treated with the dibutyl phthalate solution. The resulting lead chromate pigment is tested as described in Example 1 and the filter paper shows very intense coloration.

EXAMPLE 4

Four thousand eight hundred and seventy milliliters of an aqueous slurry containing 360 grams of the lead chromate pigment described in Example 1 is heated to 90° C. In a separate container 5.4 grams of the surfactant of Example 1 is dissolved in 54.0 grams of butyl stearate and emulsified as described in Example 1. The resulting emulsion is added dropwise over a period of 2 minutes to the aqueous slurry of pigment with agitation. Then 22 grams of aluminum sulfate is added to the slurry to effect flocculation.

To isolate the product the flocculated slurry is filtered, washed with water to a specific resistance of 2000 ohm-cm and dried at 82° C. The dried product is pulverized as described in Example 1 and yields 413 grams of bright orange pigment.

The product contains 13% by weight of butyl stearate and 87% by weight of lead chromate pigment.

The product is tested for dust as described in Example 1 and the filter paper exhibits no visible coloration.

CONTROL D

The procedure of Example 4 is followed except that no butyl stearate solution is added to the slurry. The resulting lead chromate pigment is tested as described in Example 1 and the filter paper shows very intense coloration.

What is claimed is:

1. Apparatus for collecting dust which arises from a particulate solid comprising
    a first container having an opening in the top,
    a porous member detachably fitted to said opening in the top of said first container,
    a rotatable shaft mounted transversely with respect to said first container supporting a second container for holding the particulate solid, said second container being smaller than said first container and coaxially disposed with respect to said first container, the axis of said shaft, being positioned between the top of said first container and the bottom of said first container to allow said second container to rotate within said first container, whereby the particulate solid is discharged from said second container, and
    means for applying a vacuum to said opening in the top of said first container, whereby the air-suspended particulate solid in deposited on the detachable porous member.

* * * * *